United States Patent [19]

Pederson et al.

[11] Patent Number: 4,742,035
[45] Date of Patent: May 3, 1988

[54] MIXED METAL PHOSPHORUS OXIDE CATALYSTS FOR THE OXIDATIVE DEHYDROGENATION OF CARBOXYLIC ACIDS

[75] Inventors: S. Erik Pederson, Mentor; James L. Callahan, Wooster; Harley F. Hardman, Lyndhurst, all of Ohio

[73] Assignee: The Standard Oil Co., Cleveland, Ohio

[21] Appl. No.: 7,716

[22] Filed: Jan. 28, 1987

Related U.S. Application Data

[60] Continuation of Ser. No. 668,565, Nov. 5, 1984, abandoned, which is a division of Ser. No. 408,860, Aug. 17, 1982, abandoned, which is a continuation of Ser. No. 221,859, Dec. 31, 1980, abandoned.

[51] Int. Cl.$^4$ .............. B01J 23/50; B01J 23/84; B01J 27/185
[52] U.S. Cl. .................. 502/210; 502/208; 502/213
[58] Field of Search .................. 502/208, 210, 213

[56] References Cited

U.S. PATENT DOCUMENTS

| | | | |
|---|---|---|---|
| 3,142,697 | 7/1964 | Jennings et al. | 502/208 X |
| 3,207,806 | 9/1965 | Bojars | 562/495 |
| 3,308,193 | 3/1967 | Bojars | 585/414 |
| 3,327,006 | 6/1967 | Noddings et al. | 502/210 X |
| 3,398,100 | 8/1968 | Christmann | 252/435 |
| 3,530,169 | 9/1970 | Platz et al. | 560/214 |
| 3,634,494 | 1/1972 | Tsu | 560/214 |
| 3,652,654 | 3/1972 | Tsu | 560/214 |
| 3,716,545 | 2/1973 | Ripley | 260/290 V |
| 3,832,359 | 8/1974 | Freerks et al. | 502/209 X |
| 3,855,279 | 12/1974 | Watkins | 560/214 |
| 3,862,910 | 1/1975 | Cichowski | 252/435 |
| 3,917,673 | 11/1975 | Watkins | 560/214 |
| 3,948,959 | 4/1976 | Cavaterra et al. | 562/599 |
| 3,960,767 | 6/1976 | Christmann | 252/437 |
| 3,993,591 | 11/1976 | Cichowski et al. | 252/432 |
| 4,010,114 | 3/1977 | Walker et al. | 252/437 |
| 4,026,820 | 5/1977 | Farha et al. | 252/432 |
| 4,029,695 | 6/1977 | Watkins | 560/214 |
| 4,077,912 | 3/1978 | Dolhyj et al. | 252/461 |
| 4,086,290 | 4/1978 | Cichowski et al. | 260/680 |
| 4,094,819 | 6/1978 | Betus | 252/435 |
| 4,298,755 | 11/1981 | Daniel et al. | 560/214 |
| 4,299,980 | 11/1981 | Daniel et al. | 562/599 |
| 4,324,908 | 4/1982 | Grasselli et al. | 502/208 X |
| 4,374,268 | 2/1983 | Daniel et al. | 502/213 X |
| 4,499,302 | 2/1985 | Moreschini et al. | 502/213 X |

FOREIGN PATENT DOCUMENTS

| | | | |
|---|---|---|---|
| 2438464 | 2/1975 | Fed. Rep. of Germany | 562/599 |
| 145268 | 2/1977 | India | |
| 1038432 | 8/1966 | United Kingdom | |

OTHER PUBLICATIONS

Gabel et al., "A Study of Parameters Which Affect Corrosion Between Solid Film Lubricants and Aircraft Alloys", Proc. ISLE-ASLE Int. Lubr. Conf., 1975 (Publ. 1976), pp. 804–811 [Chem. Abst. 86(12):77307p].
Rajagopalan et al., Indian Patent No. 145,268, issued 9/16/78 [Chem. Abst. 92(6):49421b].
European Patent Appln. No. 0 000 617—The Standard Oil Company—"Production of Unsubstituted and Substituted Indene".

Primary Examiner—J. Fitchett
Attorney, Agent, or Firm—M. F. Esposito; J. G. Curatolo; L. W. Evans

[57] ABSTRACT

A process is provided for the oxydehydrogenation of saturated carboxylic acids with oxygen in the presence of iron phosphorus oxide catalysts containing promoters selected from the group Ag, Al, B, Cd, Co, Cr, Cu, Ga, Ge, In, Mn, Ni, Te, Th, Ti, Tl, U, V, Zn, Zr, rare earths and mixtures thereof.

12 Claims, No Drawings

MIXED METAL PHOSPHORUS OXIDE CATALYSTS FOR THE OXIDATIVE DEHYDROGENATION OF CARBOXYLIC ACIDS

This application is a continuation of application Ser. No. 668,565, filed Nov. 5, 1984, now abandoned, which is in turn a divisional of U.S. Ser. No. 408,860, filed Aug. 17, 1982 which is a continuation of U.S. Ser. No. 221,859, filed Dec. 31, 1980, now abandoned.

BACKGROUND OF THE INVENTION

This invention relates to the catalytic, oxidative dehydrogenation of saturated carboxylic acids to their corresponding unsaturated acids. More particularly, it is directed to the production of unsaturated carboxylic acids such as methacrylic acid from saturated carboxylic acids such as isobutyric acid utilizing promoted iron phosphorus oxide catalysts.

The production of unsaturated carboxylic acids from their corresponding saturated acids using iron phosphorus oxide catalysts, with or without various promoters, is disclosed in the art.

U.S. Pat. No. 3,948,959 discloses the preparation of unsaturated acids by oxidation of the corresponding saturated acid using iron phosphorus oxide catalysts promoted with Li, Na, K, Rb, Cs, Mg, Ca, Sr and Ba. U.S. Pat. Nos. 3,634,494; 3,652,654; 3,855,279; 3,917,673 and 4,029,695 disclose the preparation of unsaturated acids and esters from saturated acids and esters using iron phosphorus oxide catalysts, containing bismuth and/or lead promoters, optionally with other promoter elements, including Mn, U, Pr, Ca, Sr, and Cr. Prior art catalysts characteristically have exhibited short life and thermal instability.

It is therefore an object of the present invention to provide a process for the production of unsaturated acids from their corresponding saturated acids.

It is a further object of the invention to provide catalysts for said process having improved catalyst life and thermal stability.

It is a further object of the invention to provide catalysts for said process having improved activity and selectivity.

SUMMARY OF THE INVENTION

We have found that unsaturated acids, particularly methacrylic acid, can be produced from their corresponding saturated acids, such as isobutyric acid, using iron phosphorus oxide catalysts promoted with particular elements, in increased yields corresponding to an increase of catalyst activity and/or selectivity over prior art catalysts. The catalysts of the present invention exhibit increased life and thermal stability with respect to the prior art catalysts.

Although promoters such as Mn, U, Cr, were disclosed as being suitable promoters in an iron lead mixed phosphate system if present in low amounts, and promoters such as Co, Ni, Cu, Zn, Cd and Ce were disclosed for that system as less than suitable promoters, we have found that these elements exhibit excellent promotional activity in the iron phosphorus oxide system for the oxydehydrogenation of saturated carboxylic acids wherein the iron phosphorus oxide is free of lead phosphate or oxide.

In general, the process of the present invention includes the preparation of unsaturated acids by contacting their corresponding saturated acids with molecular oxygen or an oxygen-containing gas in the vapor phase, at a reaction temperature of about 250° C. to 600° C. in the presence of a catalyst having the empirical formula $$A_a Fe_b P_c D_d O_x$$

wherein
A is selected from the group Al, B, Be, Cd, Co, Cr, Ga, Ge, In, Ni, Te, Th, Ti, Tl, U, V, Zn, Zr, rare earths and mixtures thereof, wherein D is selected from the group Ag, Cu, Mn and mixtures thereof, and
wherein
a=0–1.0
b=0.75–1.5
c=1.0–2.0
d=0–2.0
a+d is greater than zero, and
x is the number of oxygens needed to satisfy the valence requirements of the remaining elements.
Preferably a equals 0.15–0.5 and d equals 0.2–1.5.

The present invention further provides oxydehydrogenation catalysts having the empirical formula:

$$A_a Fe_b P_c D_d O_x$$

wherein
A is selected from the group Cd, Cr, Ge, Te, Th, Ti, U, V, Zr, rare earths and mixtures thereof;
wherein
D is selected from the group Ag, Cu, Mn and mixtures thereof, and
wherein
a=0–1.0
b=0.75–1.5
c=1.0–2.0
d=0–2.0
a+d is greater than zero, and
x is the number of oxygens needed to satisfy the valence requirements of the remaining elements.
Preferably a equals 0.15–0.5 and d equals 0.2–1.5. Preferred rare earth metal promoters are La, Ce, Nd, Sm, Eu, Dy, Ho, Tm, Yb and Lu.

DETAILED DESCRIPTION OF THE INVENTION

Saturated carboxylic acids are oxidatively dehydrogenated according to the process of the present invention in the vapor phase, in the presence of promoted iron phosphorus oxide catalysts to form the corresponding unsaturated acid. The saturated acids preferably correspond to the formula

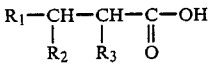

wherein $R_1$, $R_2$, and $R_3$ are each independently selected from the group consisting of hydrogen and alkyl groups containing 1 to 4 carbon atoms. The acids may contain other functional groups such as aryl or nitrile, provided the functional groups do not interfere with the dehydrogenation reaction, under the reaction conditions required. The dehydrogenation occurs essentially in the alpha, beta position.

The process of the present invention is highly suitable for the oxidative dehydrogenation of isobutyric acid to methacrylic acid.

The promoted iron phosphorus oxide catalysts of the present invention are represented by the formula set forth above. These catalysts may be prepared according to methods known in the art.

One method of preparing the catalysts of the present invention includes introducing a compound of iron, and a compound containing the promoter element into water and contacting with a phosphorus compound, or the iron and promoter containing compound are introduced into an aqueous solution of phosphoric acid. Preferably, the compounds used containing iron and the promoter elements are soluble in water, and may include salts such as nitrates, halides, sulfates, acetates, carbonates, formates and the like. The resulting solution or slurry is evaporated to dryness, and the resulting solid is calcined at from about 300° to 700° C. Alternatively, the catalyst may be prepared in an organic liquid medium. Alternatively, the aqueous solution or slurry can be adjusted to a pH of about 5-6 before drying.

The catalyst may be formed into tablets, pellets and the like, and may be prepared for use in either fixed or fluid beds. The catalyst may be combined with inert diluents such as silica. Alternately, the catalyst may be coated upon inert supports, such as silica, alumina, alumina-silica, silicon carbide, titania, zirconia, zeolites and clays such as kieselguhr. Techniques of coating are included in U.S. Pat. No. 4,077,912, The inert supports preferably are of at least about 20 microns in diameter.

The promoted iron phosphorus oxide catalysts of the present invention exhibit enhanced activity and selectivity for the oxydehydrogenation of saturated carboxylic acids, particularly isobutyric acid. The catalysts also exhibit long life and thermal stablity.

The saturated acids are contacted with the catalyst in the vapor phase, together with molecular oxygen. The molecular oxygen is most conveniently added as air, but synthetic streams containing oxygen are also suitable. In addition to the carboxylic acid feed and molecular oxygen, other gases may be added to the reactant feed. For example, steam is preferably added to the reactant feed to aid in the reaction, although the mechanism by which it does so is not certain. Inert diluents such as nitrogen, carbon monoxide, carbon dioxide and argon may also be added.

The molar ratio of the reactants may vary widely and are not critical. The ratios of carboxylic acid:air:steam are in the range of 1:2.5-50:0-50 and are preferably 1:3-10:10-30. Diluents may be present in the range of 0-40 moles per mole of carboxylic acid.

The reaction temperature may vary widely and is dependent upon the particular carboxylic acid and catalyst employed. Normally, temperatures of about 250° to 600° C. are employed with temperatures of 325°-450° C. being preferred.

The contact time may vary from a fraction of a second to about 50 seconds. In fixed bed reactions the contact time is preferably about 0.5 seconds to about 10 seconds, for fluid bed, preferably from about 2 seconds to about 20 seconds. The reaction may be conducted at atmospheric, superatmospheric or subatmospheric pressure, preferably from about 1 psia to about 100 psia, most preferably between about 10 to about 30 psia.

In the production of methacrylic acid from isobutyric acid, the major by-product is acetone (generally about 5-15% yield) which may be removed from the product by conventional methods.

SPECIFIC EMBODIMENTS OF THE INVENTION

Catalysts tested in the below examples were prepared according to the following procedure.

$Fe(NO_3)_3 \cdot 9H_2O$, the appropriate promoter metal nitrate and $H_3PO_4$ (85%) were added to water in the amounts necessary to provide the molar ratios set forth in the tables below, for each of the particular catalysts reported. The solution of the components was evaporated to a dry paste with heating and stirring. The paste was dried for about 16 hours at 110° C., and the resulting solid was calcined for about 2 hours at 540° C. The solid was crushed and screened to 14-30 mesh (0.595-1.41 mm).

The catalyst particles were processed according to the examples below, and were tested for the oxydehydrogenation of isobutyric acid to methacrylic acid in a 20 cc fixed bed reactor. The reactor consisted of a length of stainless steel tubing having an outer diameter of about 1.3 cm, and containing a full length 0.31 cm diameter axial thermowell. The reactor was heated with a split stainless steel block furnace.

The isobutyric acid was fed to the reactor by passing air through a saturator filled with isobutyric acid and maintained at a temperature of 108° C. Water was fed by means of a tubing pump and vaporized in a compartment maintained at about 154° C. before entering the reactor. Liquid products were analyzed on a Hewlett Packard 5710 A F.I.D. gas chromatograph. Gaseous products were analyzed on a conventional split column system.

The test reactions were run a atmospheric pressure, unless otherwise noted. Reaction conditions such as temperature, feed ratios, contact time and catalyst working rate (WWH=weight of isobutyric acid/weight of catalyst/hour) are listed in the tables below. Results of the tests reported in the tables below are reported in terms as follows:

$$\text{Single Pass Yield} = \frac{\text{Moles of Methacrylic Acid Formed} \times 100}{\text{Moles of Isobutyric Acid Fed}}$$

$$\text{Total Conversion} = \frac{\text{Moles of Isobutyric Acid Reacted} \times 100}{\text{Moles of Isobutyric Acid Fed}}$$

$$\text{Selectivity} = \frac{\text{Single Pass Yield} \times 100}{\text{Total Conversion}}$$

100% Active Catalysts

Examples 1-13

Iron phosphorus oxide catalysts promoted with manganese (added as manganese nitrate) in varying molar ratios were prepared according to the procedure set forth above. The crushed and screened catalysts were charged to the reactor. The results of the tests, together with the amount of manganese in the catalysts are reported in Table I.

Examples 14-39

Iron phosphorus oxide catalysts promoted with silver (added as silver nitrate) in varying amounts were prepared according to the procedure set forth above. The crushed and screened catalysts were charged to the reactor. The results of the tests, together with the amount of silver in the catalysts are reported in Table II.

Examples 40-50

Iron phosphorus oxide catalysts promoted with copper (added as copper nitrate) in varying amounts were prepared according to the procedure set forth above. The crushed and screened catalysts were charged to the reactor. The results of the tests, together with the amount of copper in the catalysts are reported in Table III.

Examples 51-62

Catalysts of the formula $TH_{0.2}Fe_1P_{1.84}O_x$ were prepared from iron and thorium nitrates according to the procedure set forth above. The crushed and screened catalysts were charged to the reactor. The results of the tests are reported in Table IV.

Examples 63-118

Catalysts having the formula $A_aFe_1P_{1.84}O_x$ were prepared with the designated promoter metal nitrates as set forth in the procedure above, The crushed and screened catalysts were charged to the reactor. The results of the tests and the amount and identity of the promoter metal are reported in Table V.

Examples 119-124

Catalysts having the formula $A_aFe_1P_{1.84}D_dO_x$ containing two promoter elements were prepared as set forth in the procedure above. The crushed and screened catalysts were charged to the reactor. The results of the tests and the amounts and identities of the promoters are reported in Table VI.

Diluent-containing catalysts

Examples 125-132

Catalysts having the formula $Ag_{0.8}Fe_1P_{1.84}O_x$ were prepared according to the procedure set forth above, with the addition of various amounts of silica to the catalyst during preparation by slurrying in water. The crushed and screened catalysts were charged to the reactor. The results of the tests and the weight percents of active material and silica are reported in Table VII.

Coated Catalysts

Examples 133-140

Catalysts of the formula $A_aFe_{1.0}P_{1.84}O_x$ were prepared according to the procedure set forth above. The crushed and screened catalysts were ground to a fine powder, and coated upon Alundum SA 5209 spheres (trade designation of Norton Company) according to the method set forth in U.S. Pat. No. 4,077,912, with water as the wetting agent. The results of the tests, the catalyst used and the weight percent of catalyst loading (based upon total weight) are reported in Table VIII.

Examples 141-150

Catalysts of the formula $A_{0.6}Fe_{1.0}P_{1.8}O_x$ were prepared according to the procedure set forth above, except that the pH of the aqueous solution was adjusted to about 6 by addition of concentrated $NH_4OH$ solution. The dried catalysts were ground to a fine powder and coated on Alundum which had been ground to 10-20 mesh, using the method set forth in U.S. Pat. No. 4,077,912 with absolute ethanol as a wetting agent. The coated particles were dried at 175° C. for 30 minutes and calcined for 2 hours at 540° C. The catalyst loading was about 17 weight percent.

The catalysts were tested in a 5 cc reactor consisting of a 6½" (16.5 cm) stainless steel tube of 5/16" (0.8 cm) inner diameter immersed in a molten salt bath. Feed ratios were 1 IBA/5 AIR/25 $H_2O$ at a contact time of about 2 seconds. Reaction temperature was 415° C. Run time was about one hour. Results of the tests and the identity of the promoter elements contained in the catalysts are listed in Table IX.

We have found that the iron phosphorus oxide catalysts, promoted according to the present invention, are not particularly suited to the oxydehydrogenation of saturated carboxylic acid esters, due to the hydrolysis of the ester by water formed as a by-product of the reaction even if steam is not co-fed. The oxydehydrogenation of the ester with these catalysts generally results either primarily in the formation of the unsaturated acid, or in low conversions to both acid and ester.

A catalyst of the formula $Th_{0.2}Fe_{1.0}P_{1.84}O_x$ was prepared according to the procedure of examples 51-62. Methyl isobutyrate was oxydehydrogenated over this catalyst in the 20 cc reactor described above at 444° C. with a feed ratio of $MIBA/AIR/H_2O/N_2$ equals 1/4.5/18/7.8 and a contact time of 1.6 seconds. Total conversion was 95.6%, but yield of methyl methacrylate was only 11.6% with a yield of methacrylic acid of 38.6%. With no steam being co-fed, (replaced by nitrogen), yield of methyl methacrylate increased to 23%, but total conversion decreased to 47.8%.

As is demonstrated by the test results reported in Tables I through IX, promoted iron phosphorus oxide catalysts according to the present invention exhibit high activity and selectivity in the oxydehydrogenation of saturated carboxylic acids, particularly isobutyric acid, to the corresponding unsaturated acid. The catalysts of the invention additionally exhibit long life and thermal stability, as is demonstrated by the test results reported in the tables.

Thus it should be apparent to those skilled in the art that the subject invention accomplishes the objects set forth above. It is to be understood that the subject invention is not to be limited by the examples set forth herein. These have been provided merely to demonstrate operability, and the selection of iron and phosphorus-containing compounds, promoter element-containing compounds, preparation techniques, reaction feedstocks and reaction conditions can be determined from the total specification disclosure provided without departing from the spirit of the invention herein disclosed and described, the scope of the invention including modifications and variations that fall within the scope of the attached claims.

TABLE I

OXYDEHYDROGENATION OF ISOBUTYRIC ACID TO METHACRYLIC ACID OVER $Mn_aFe_{1.0}P_{1.84}O_x$ CATALYSTS

| Example No. | Molar Ratio-Mn (a) | Feed Ratio IBA/Air/$H_2O$ | Temperature °C. | Contact Time (Sec.) | WWH | Methacrylic Acid % Yield | Methacrylic Acid % Selectivity | % Conversion | Hours On Stream |
|---|---|---|---|---|---|---|---|---|---|
| 1 | 0.33 | 1/4.8/24.7 | 429 | 0.9 | 0.3 | 58.7 | 64.1 | 91.6 | 22 |
| 2 | 0.33 | 1/4.8/24.7 | 447 | 0.9 | 0.3 | 54.9 | 57.0 | 96.4 | 41 |
| 3 | 0.33 | 1/4.1/24.7 | 410 | 1.0 | 0.34 | 76.1 | 76.9 | 98.9 | 22.5 |

TABLE I-continued
OXYDEHYDROGENATION OF ISOBUTYRIC ACID TO METHACRYLIC ACID OVER $Mn_aFe_{1.0}P_{1.84}O_x$ CATALYSTS

| Example No. | Molar Ratio-Mn (a) | Feed Ratio IBA/Air/H₂O | Temperature °C. | Contact Time (Sec.) | WWH | Methacrylic Acid % Yield | % Selectivity | % Conversion | Hours On Stream |
|---|---|---|---|---|---|---|---|---|---|
| 4 | 0.33 | 1/4.1/24.7 | 410 | 1.0 | 0.34 | 74.6 | 75.4 | 98.8 | 47 |
| 5 | 0.5 | 1/4.4/24.7 | 393 | 1.0 | 0.34 | 76.2 | 77.6 | 98.3 | 36 |
| 6 | 0.5 | 1/3.4/24.7 | 390 | 1.0 | 0.34 | 76.7 | 81.8 | 93.8 | 58.5 |
| 7 | 0.5 | 1/3.7/24.7 | 419 | 1.0 | 0.34 | 79.3 | 81.5 | 97.3 | 114.5 |
| 8 | 0.7 | 1/4.1/24.7 | 368 | 1.0 | 0.51 | 77.8 | 79.7 | 97.5 | 24.5 |
| 9 | 0.7 | 1/3.3/24.7 | 397 | 1.0 | 0.51 | 77.8 | 81.5 | 95.4 | 50.5 |
| 10 | 0.7 | 1/3.7/24.7 | 409 | 1.0 | 0.51 | 74.9 | 79.1 | 94.7 | 73.5 |
| 11 | 1.0 | 1/4.7/32.3 | 399 | 0.7 | 0.40 | 67.9 | 70.8 | 95.9 | 22 |
| 12 | 1.0 | 1/4.7/37.3 | 389 | 0.7 | 0.40 | 68.2 | 69.7 | 93.5 | 45 |
| 13 | 1.0 | 1/4.7/25.3 | 413 | 0.9 | 0.40 | 63.8 | 69.1 | 92.4 | 54 |

TABLE II
OXYDEHYDROGENATION OF ISOBUTYRIC ACID TO METHACRYLIC ACID OVER $Ag_aFe_{1.0}P_{1.84}O_x$ CATALYSTS

| Example No. | Molar Ratio-Ag (a) | Feed Ratio IBA/Air/H₂O | Temperature °C. | Contact Time (Sec.) | WWH | Methacrylic Acid % Yield | % Selectivity | % Conversion | Hours On Stream |
|---|---|---|---|---|---|---|---|---|---|
| 14 | 0.33 | 1/4.7/24.7 | 385 | 1.0 | 0.23 | 67.7 | 75.3 | 89.9 | 24.4 |
| 15 | 0.33 | 1/4.8/24.7 | 382 | 1.0 | 0.23 | 69.0 | 70.2 | 98.3 | 52.5 |
| 16 | 0.33 | 1/4.8/24.7 | 378 | 1.0 | 0.23 | 66.8 | 69.2 | 96.6 | 73.6 |
| 17 | 0.66 | 1/4.9/25.3 | 406 | 0.9 | 0.27 | 71.9 | 71.9 | 100 | 24.6 |
| 18 | 0.66 | 1/4.4/25.3 | 382 | 1.0 | 0.27 | 74.3 | 76.1 | 97.5 | 50.9 |
| 19 | 0.70 | 1/4.5/25.3 | 387 | 1.0 | 0.18 | 73.8 | 76.1 | 96.9 | 45.9 |
| 20 | 0.75 | 1/4.8/24.7 | 368 | 1.0 | 0.20 | 74.9 | 80.8 | 92.7 | 24 |
| 21 | 0.75 | 1/5/24.7 | 388 | 1.0 | 0.20 | 80.0 | 81.1 | 98.7 | 36 |
| 22 | 0.75 | 1/5.5/25.6 | 391 | 0.9 | 0.20 | 80.2 | 82.1 | 97.6 | 108 |
| 23 | 0.75 | 1/5/17.3 | 407 | 1.2 | 0.20 | 70.6 | 72.9 | 96.8 | 198 |
| 24 | 0.75 | 1/5/30.5 | 390 | 0.8 | 0.20 | 75.1 | 76.8 | 97.8 | 243 |
| 25 | 0.8 | 1/4.5/24.7 | 388 | 1.0 | 0.19 | 78.4 | 79.6 | 98.5 | 46.5 |
| 26 | 0.8 | 1/3.6/24.7 | 395 | 1.0 | 0.19 | 80.4 | 82.2 | 97.8 | 83 |
| 27 | 0.8 | 1/4.7/24.7 | 406 | 1.0 | 0.19 | 73.1 | 73.1 | 100 | 156 |
| 28 | 0.8 | 1/4.8/24.7 | 383 | 1.0 | 0.19 | 73.1 | 75.1 | 97.3 | 244 |
| 29 | 0.8 | 1/4.8/17.5 | 390 | 1.3 | 0.19 | 70.9 | 74.4 | 95.3 | 250 |
| 30 | 0.85 | 1/5.5/24.7 | 368 | 1.0 | 0.18 | 73.6 | 76.7 | 95.9 | 54.5 |
| 31 | 0.85 | 1/4.8/24.7 | 368 | 1.0 | 0.18 | 81.4 | 84.5 | 96.3 | 84 |
| 32 | 0.85 | 1/4.5/24.7 | 370 | 1.1 | 0.18 | 77.6 | 80.7 | 96.2 | 127 |
| 33* | 0.8 | 1/5/26.2 | 376 | 0.9 | 0.26 | 74.7 | 76.3 | 99.2 | 24 |
| 34* | 0.8 | 1/4.1/26.2 | 373 | 0.9 | 0.26 | 76.3 | 78.4 | 97.3 | 48.5 |
| 35* | 0.8 | 1/3.6/32.9 | 376 | 0.8 | 0.26 | 79.9 | 81.9 | 97.6 | 59.5 |
| 36 | 1.0 | 1/4.7/24.7 | 386 | 1.0 | 0.22 | 73.7 | 76.1 | 96.9 | 26.5 |
| 37 | 1.0 | 1/4.7/24.7 | 389 | 1.0 | 0.22 | 71.0 | 78.2 | 90.8 | 52 |
| 38 | 1.0 | 1/4.8/24.7 | 360 | 1.1 | 0.14 | 70.4 | 72.7 | 97.0 | 24 |
| 39 | 1.5 | 1/5/24.7 | 366 | 1.0 | 0.13 | 69.4 | 71.2 | 97.4 | 25.8 |

*Molar ratio Fe = 1.2

TABLE III
OXYDEHYDROGENATION OF ISOBUTYRIC ACID TO METHACRYLIC ACID OVER $Cu_aFe_{1.0}P_{1.84}O_x$ CATALYSTS

| Example No. | Molar Ratio-Cu (a) | Feed Ratio IBA/Air/H₂O | Temperature °C. | Contact Time (Sec.) | WWH | Methacrylic Acid % Yield | % Selectivity | % Conversion | Hours On Stream |
|---|---|---|---|---|---|---|---|---|---|
| 40 | 0.2 | 1/4.8/24.7 | 405 | 1.0 | 0.27 | 68.1 | 72.1 | 94.4 | 24 |
| 41 | 0.2 | 1/4.8/24.7 | 387 | 1.0 | 0.27 | 70.0 | 72.1 | 97.1 | 46 |
| 42 | 0.33 | 1/4.8/24.7 | 396 | 1.0 | 0.28 | 66.2 | 66.3 | 99.9 | 27 |
| 43 | 0.33 | 1/4.9/24.7 | 386 | 1.0 | 0.28 | 67.1 | 71.2 | 94.3 | 72 |
| 44* | 0.33 | 1/4.3/22.0 | 374 | 1.7 | 0.32 | 65.7 | 69.9 | 94.0 | 107 |
| 45 | 0.66 | 1/4.8/24.7 | 368 | 1.0 | 0.26 | 70.9 | 72.9 | 97.3 | 25 |
| 46 | 0.66 | 1/4.8/24.7 | 368 | 1.0 | 0.26 | 71.4 | 74.0 | 96.6 | 49 |
| 47* | 0.66 | 1/4.8/13.0 | 410 | 0.9 | 0.77 | 61.9 | 67.0 | 92.4 | 60 |
| 48* | 0.66 | 1/4.2/22.6 | 386 | 0.9 | 0.52 | 68.1 | 72.6 | 93.8 | 67 |
| 49* | 0.66 | 1/4.7/12.9 | 430 | 0.9 | 0.77 | 63.1 | 68.1 | 92.8 | 76 |
| 50 | 1.0 | 1/4.9/24.7 | 429 | 0.9 | 0.27 | 49.5 | 55.9 | 88.5 | 24 |

*Run at reactor outlet pressure 12 PSIG.

TABLE IV
OXYDEHYDROGENATION OF ISOBUTYRIC ACID TO METHACRYLIC ACID OVER $Th_{0.2}Fe_{1.0}P_{1.84}O_x$ CATALYSTS

| Example No. | Feed Ratio IBA/Air/H₂O | Temperature °C. | Contact Time (Sec.) | WWH | Methacrylic Acid % Yield | % Selectivity | % Conversion | Hours On Stream |
|---|---|---|---|---|---|---|---|---|
| 51 | 1/5/11 | 400 | 1.7 | 0.34 | 71.0 | 71.2 | 99.8 | 39 |
| 52 | 1/5/11 | 398 | 1.7 | 0.34 | 67.5 | 70.6 | 95.6 | 68 |

TABLE IV-continued

OXYDEHYDROGENATION OF ISOBUTYRIC ACID TO METHACRYLIC ACID OVER $Th_{0.2}Fe_{1.0}P_{1.84}O_x$ CATALYSTS

| Example No. | Feed Ratio IBA/Air/H$_2$O | Temperature °C. | Contact Time (Sec.) | WWH | Methacrylic Acid % Yield | % Selectivity | % Conversion | Hours On Stream |
|---|---|---|---|---|---|---|---|---|
| 53 | 1/5/11 | 402 | 1.7 | 0.34 | 60.5 | 65.4 | 92.5 | 136 |
| 54 | 1/5/15 | 402 | 1.4 | 0.34 | 66.9 | 69.0 | 96.9 | 203 |
| 55 | 1/4/20 | 413 | 1.1 | 0.34 | 66.7 | 72.9 | 91.5 | 330 |
| 56 | 1/4/26 | 423 | 0.9 | 0.34 | 65.7 | 71.2 | 92.2 | 401 |
| 57 | 1/5.5/26 | 412 | 0.9 | 0.34 | 63.3 | 67.1 | 94.3 | 499 |
| 58 | 1/5/24 | 397 | 1.0 | 0.34 | 61.0 | 70.9 | 86.0 | 616 |
| 59 | 1/5/24 | 406 | 1.0 | 0.34 | 65.3 | 68.9 | 94.7 | 809 |
| 60 | 1/5/25 | 426 | 1.4 | 0.22 | 57.9 | 66.4 | 87.2 | 979 |
| 61 | 1/5/25 | 407 | 0.9 | 0.34 | 70.2 | 71.6 | 98.1 | 1,045 |
| 62 | 1/5/25 | 402 | 1.0 | 0.34 | 68.8 | 69.4 | 99.1 | 1,074 |

TABLE V

OXYDEHYDROGENATION OF ISOBUTYRIC ACID TO METHACRYLIC ACID OVER $A_aFe_{1.0}P_{1.84}O_x$ CATALYSTS

| Example No. | Promoter & Mole Ratio (Aa) | Feed Ratio IBA/Air/H$_2$O | Temperature °C. | Contact Time (Sec.) | WWH | Methacrylic Acid % Yield | % Selectivity | % Conversion | Hours On Stream |
|---|---|---|---|---|---|---|---|---|---|
| 63 | Ce$_{0.2}$ | 1/5/31 | 391 | 1.8 | 0.18 | 53.8 | 57.0 | 94.3 | 8 |
| 64 | Ce$_{0.2}$ | 1/8/50 | 390 | 1.8 | 0.11 | 58.7 | 59.7 | 98.3 | 16 |
| 65 | Co$_{0.33}$ | 1/4.8/24.7 | 428 | 0.9 | 0.28 | 61.0 | 65.1 | 93.8 | 19 |
| 66 | Co$_{0.33}$ | 1/4.8/24.7 | 446 | 0.9 | 0.28 | 61.9 | 64.0 | 96.6 | 55 |
| 67 | Co$_{0.33}$ | 1/3.9/26.1 | 432 | 0.9 | 0.29 | 70.9 | 74.0 | 95.9 | 24 |
| 68 | Co$_{0.33}$ | 1/3.9/26.1 | 442 | 0.9 | 0.29 | 69.2 | 73.5 | 94.2 | 50 |
| 69 | Cr$_{0.22}$ | 1/4.8/24.7 | 425 | 0.9 | 0.36 | 55.6 | 60.5 | 92.0 | 50 |
| 70 | Cr$_{0.22}$ | 1/4.8/24.7 | 425 | 0.9 | 0.36 | 49.1 | 63.7 | 91.5 | 70 |
| 71 | Cr$_{0.22}$ | 1/4.6/26.1 | 432 | 0.9 | 0.36 | 65.3 | 68.3 | 95.5 | 23 |
| 72 | Cr$_{0.22}$ | 1/5/26.1 | 423 | 0.9 | 0.36 | 67.0 | 67.8 | 98.8 | 36 |
| 73 | Dy$_{0.22}$ | 1/5/25 | 411 | 1.0 | 0.23 | 65.8 | 66.7 | 98.7 | 47 |
| 74 | Dy$_{0.22}$ | 1/5/25 | 417 | 0.9 | 0.23 | 65.6 | 68.5 | 95.7 | 74 |
| 75 | Eu$_{0.22}$ | 1/5/25 | 407 | 0.9 | 0.28 | 63.5 | 65.8 | 96.5 | 24 |
| 76 | Eu$_{0.22}$ | 1/5/25 | 407 | 0.9 | 0.28 | 62.3 | 65.7 | 94.9 | 41 |
| 77 | Eu$_{0.22}$ | 1/4.6/26.1 | 396 | 0.9 | 0.29 | 68.1 | 72.5 | 93.9 | 31 |
| 78 | Ge$_{0.2}$ | 1/4/26 | 412 | 1.7 | 0.22 | 48.5 | 52.6 | 92.3 | |
| 79 | Ge$_{0.2}$ | 1/4/25 | 418 | 1.7 | 0.22 | 54.8 | 57.3 | 95.7 | |
| 80 | Ho$_{0.22}$ | 1/4.8/24.7 | 412 | 0.9 | 0.26 | 58.4 | 61.7 | 94.6 | 40 |
| 81 | Ho$_{0.22}$ | 1/4.8/24.7 | 414 | 0.9 | 0.26 | 54.1 | 63.6 | 85.1 | 57 |
| 82 | Ho$_{0.22}$ | 1/5/26.1 | 434 | 0.9 | 0.27 | 63.4 | 64.2 | 98.7 | 24 |
| 83 | Ho$_{0.22}$ | 1/4.9/26.1 | 424 | 0.9 | 0.27 | 67.3 | 69.0 | 97.6 | 54 |
| 84 | La$_{0.22}$ | 1/5.4/24.7 | 424 | 0.9 | 0.3 | 63.5 | 66.0 | 96.2 | 26 |
| 85 | La$_{0.22}$ | 1/5.4/24.7 | 425 | 0.9 | 0.3 | 64.2 | 66.4 | 96.7 | 30 |
| 86 | Lu$_{0.22}$ | 1/4.8/24.7 | 424 | 0.9 | 0.30 | 59.2 | 62.5 | 94.8 | 27 |
| 87 | Lu$_{0.22}$ | 1/4.8/24.7 | 434 | 0.9 | 0.30 | 53.7 | 63.0 | 85.3 | 50 |
| 88 | Nd$_{0.22}$ | 1/4/23 | 396 | 1.7 | 0.17 | 60.3 | 62.9 | 95.8 | 7 |
| 89 | Nd$_{0.22}$ | 1/4/24 | 402 | 1.7 | 0.17 | 65.4 | 70.3 | 93.1 | 30 |
| 90 | Ni$_{0.33}$ | 1/4.8/24.7 | 432 | 0.9 | 0.33 | 57.2 | 60.7 | 94.2 | 25 |
| 91 | Ni$_{0.33}$ | 1/4.8/26.1 | 428 | 0.9 | 0.32 | 64.7 | 64.8 | 99.8 | 25 |
| 92 | Ni$_{0.33}$ | 1/4.8/26.1 | 418 | 0.9 | 0.32 | 69.1 | 69.7 | 99.2 | 50 |
| 93 | Ni$_{0.33}$ | 1/3.7/26.1 | 413 | 0.9 | 0.32 | 73.2 | 75.1 | 97.5 | 71 |
| 94 | Sm$_{0.22}$ | 1/4.4/25.3 | 425 | 0.9 | 0.27 | 66.7 | 67.6 | 98.7 | 25 |
| 95 | Sm$_{0.22}$ | 1/4.8/25.3 | 432 | 0.9 | 0.27 | 66.2 | 69.0 | 96.0 | 49 |
| 96 | Ti$_{0.2}$ | 1/4/22 | 409 | 1.6 | 0.26 | 63.1 | 66.7 | 94.6 | 6 |
| 97 | Ti$_{0.2}$ | 1/4/28 | 413 | 1.3 | 0.26 | 58.2 | 62.2 | 93.6 | 12 |
| 98[b] | Th$_{0.2}$ | 1/4.1/25.3 | 410 | 1.0 | 0.28 | 75.1 | 75.8 | 99.0 | 23 |
| 99[b] | Th$_{0.2}$ | 1/3.7/25.3 | 410 | 1.0 | 0.28 | 76.3 | 77.4 | 98.6 | 48 |
| 100[c] | Th$_{0.2}$ | 1/4.8/25.3 | 417 | 0.9 | 0.34 | 71.6 | 72.6 | 98.6 | 23 |
| 101[c] | Th$_{0.2}$ | 1/3.8/25.3 | 419 | 1.0 | 0.34 | 73.6 | 74.8 | 98.4 | 35 |
| 102[d] | Th$_{0.2}$ | 1/4.8/25.3 | 392 | 1.0 | 0.25 | 68.8 | 68.9 | 99.9 | 24 |
| 103[d] | Th$_{0.2}$ | 1/3.5/25.3 | 382 | 1.0 | 0.24 | 76.2 | 77.2 | 98.6 | 44 |
| 104 | Tm$_{0.22}$ | 1/4.8/24.7 | 412 | 0.9 | 0.27 | 60.1 | 65.3 | 92.0 | 25 |
| 105 | Tm$_{0.22}$ | 1/4.8/24.7 | 423 | 0.9 | 0.27 | 56.4 | 62.7 | 89.9 | 46 |
| 106 | U$_{0.3}$ | 1/3.3/24.7 | 404 | 1.0 | 0.21 | 78.0 | 80.9 | 96.4 | 24 |
| 107 | U$_{0.2}$ | 1/5.4/24.7 | 418 | 0.9 | 0.23 | 71.1 | 71.2 | 99.9 | 25 |
| 108 | U$_{0.2}$ | 1/4.9/24.7 | 394 | 0.9 | 0.23 | 74.2 | 75.0 | 98.9 | 48 |
| 109 | U$_{0.2}$ | 1/5.3/24.7 | 395 | 0.9 | 0.23 | 72.5 | 73.0 | 99.2 | 67 |
| 110 | U$_{0.2}$ | 1/4.7/24.7 | 382 | 1.0 | 0.23 | 75.0 | 76.5 | 98.0 | 73 |
| 111 | U$_{0.2}$ | 1/4.0/24.7 | 388 | 1.0 | 0.23 | 76.1 | 77.7 | 98.0 | 99 |
| 112 | V$_{0.22}$ | 1/4.8/25 | 391 | 1.0 | 0.41 | 50.1 | 51.1 | 98.1 | 25 |
| 113 | V$_{0.22}$ | 1/4.7/25 | 382 | 1.0 | 0.41 | 49.8 | 52.2 | 95.4 | 45 |
| 114 | Yb$_{0.22}$ | 1/4/23 | 392 | 1.7 | 0.18 | 64.5 | 68.4 | 94.3 | 6 |
| 115 | Yb$_{0.22}$ | 1/4/25 | 396 | 1.7 | 0.28 | 61.1 | 66.3 | 92.2 | 15 |
| 116 | Zn$_{0.33}$ | 1/4/25 | 442 | 1.6 | 0.2 | 58.4 | 60.3 | 96.9 | 10 |
| 117 | Zr$_{0.2}$ | 1/5/23 | 398 | 1.7 | 0.16 | 65.1 | 66.7 | 97.6 | 5 |

TABLE V-continued
OXYDEHYDROGENATION OF ISOBUTYRIC ACID TO METHACRYLIC ACID OVER $A_aFe_{1.0}P_{1.84}O_x$ CATALYSTS

| Example No. | Promoter & Mole Ratio (Aa) | Feed Ratio IBA/Air/H$_2$O | Temperature °C. | Contact Time (Sec.) | WWH | Methacrylic Acid % Yield | % Selectivity | % Conversion | Hours On Stream |
|---|---|---|---|---|---|---|---|---|---|
| 118 | Zr$_{0.2}$ | 1/4/22 | 398 | 1.7 | 0.16 | 65.6 | 70.0 | 93.7 | 7 |

[b]molar ratio Fe = 1.2
[c]Molar ratio Fe = 0.8
[d]Molar ratio P = 1.5

TABLE VI
OXYDEHYDROGENATION OF ISOBUTYRIC ACID TO METHACRYLIC ACID OVER $AaFe_{1.0}P_{1.84}DdO_x$ CATALYSTS

| Example No. | Promoter & Mole Ratio (AaDd) | Feed Ratio IBA/Air/H$_2$O | Temperature °C. | Contact Time (Sec.) | WWH | Methacrylic Acid % Yield | % Selectivity | % Conversion | Hours On Stream |
|---|---|---|---|---|---|---|---|---|---|
| 119 | Ag$_{0.4}$Mn$_{0.4}$ | 1/4.3/26.1 | 400 | 0.9 | 0.29 | 75.1 | 75.4 | 99.6 | 19 |
| 120 | Ag$_{0.4}$Mn$_{0.4}$ | 1/4.3/26.1 | 385 | 0.9 | 0.29 | 74.7 | 76.4 | 97.8 | 24 |
| 121 | Ag$_{0.4}$Mn$_{0.4}$ | 1/4.1/36.8 | 385 | 0.7 | 0.29 | 74.1 | 77.8 | 95.3 | 44 |
| 122 | Ag$_{0.5}$U$_{0.3}$ | 1/4.5/25.3 | 387 | 1.0 | 0.18 | 74.6 | 75.9 | 98.3 | 20 |
| 123 | Ag$_{0.5}$U$_{0.3}$ | 1/4.5/25.3 | 377 | 1.0 | 0.18 | 73.7 | 76.9 | 95.8 | 23 |
| 124 | Ag$_{0.5}$U$_{0.3}$ | 1/4.5/25.3 | 382 | 1.0 | 0.18 | 74.2 | 75.8 | 97.9 | 43 |

TABLE VII
OXYDEHYDROGENATION OF ISOBUTYRIC ACID TO METHACRYLIC ACID OVER $Ag_{0.8}Fe_{1.0}P_{1.84}O_x$ WITH SILICA DILUENTS

| Example No. | Weight Percent Diluent | Feed Ratio IBA/Air/H$_2$O | Temperature °C. | Contact Time (Sec.) | WWH | Methacrylic Acid % Yield | % Selectivity | % Conversion | Hours On Stream |
|---|---|---|---|---|---|---|---|---|---|
| 125 | 20 | 1/4.8/26.1 | 415 | 0.9 | 0.16 | 75.0 | 76.1 | 98.6 | 26 |
| 126 | 20 | 1/4.2/26.1 | 419 | 0.9 | 0.16 | 74.5 | 76.3 | 97.6 | 39 |
| 127 | 20 | 1/4.0/25.3 | 388 | 1.0 | 0.23 | 77.0 | 79.1 | 97.3 | 49 |
| 128 | 30 | 1/4.4/25.3 | 380 | 1.0 | 0.23 | 72.6 | 73.4 | 98.8 | 25 |
| 129 | 30 | 1/3.8/25.3 | 375 | 1.0 | 0.23 | 73.5 | 75.8 | 96.9 | 53 |
| 130 | 40 | 1/4.5/25.3 | 382 | 1.0 | 0.25 | 73.5 | 76.0 | 96.7 | 25 |
| 131 | 40 | 1/3.9/25.3 | 394 | 1.0 | 0.25 | 75.1 | 76.6 | 98.1 | 49 |
| 132 | 50 | 1/4.6/25.3 | 397 | 0.9 | 0.26 | 70.4 | 71.8 | 98.5 | 24 |

TABLE VIII
OXYDEHYDROGENATION OF ISOBUTYRIC ACID TO METHACRYLIC ACID OVER COATED CATALYSTS

| Example No. | Weight % Active | Feed Ratio IBA/Air/H$_2$O | Temperature °C. | Contact Time (Sec.) | WWH | Methacrylic Acid % Yield | % Selectivity | % Conversion | Hours On Stream |
|---|---|---|---|---|---|---|---|---|---|
| | | | $Ag_{0.8}Fe_{1.0}P_{1.84}O_x$ on 10-30 mesh alundum | | | | | | |
| 133 | 16.4 | 1/4.1/24.7 | 445 | 0.9 | 0.18 | 76.0 | 77.2 | 98.4 | 23 |
| 134 | 16.4 | 1/3.8/36.8 | 434 | 0.7 | 0.18 | 69.2 | 75.3 | 91.9 | 31 |
| 135 | 30 | 1/3.9/26.1 | 427 | 0.9 | 0.15 | 78.2 | 82.6 | 94.7 | 24 |
| 136 | 30 | 1/4/26.1 | 432 | 0.9 | 0.15 | 79.0 | 81.7 | 96.7 | 36 |
| | | | $Mn_{0.5}Fe_{1.0}P_{1.84}O_x$ on ⅛ inch alundum | | | | | | |
| 137 | 35 | 1/5/25.9 | 409 | 0.9 | 0.21 | 69.5 | 72.2 | 96.2 | 23 |
| 138 | 35 | 1/4.7/25.3 | 421 | 0.9 | 0.21 | 66.8 | 67.7 | 98.7 | 48 |
| 139 | 45 | 1/4.8/26.1 | 414 | 0.9 | 0.22 | 64.9 | 66.2 | 98.0 | 26 |
| 140 | 45 | 1/4.2/36 | 430 | 0.7 | 0.22 | 66.6 | 67.4 | 98.9 | 34 |

TABLE IX
OXYDEHYDROGENATION OF ISOBUTYRIC ACID TO METHACRYLIC ACID OVER 17 WEIGHT PERCENT COATED $A_aFe_{1.0}P_{1.8}O_x$ ON ALUNDUM

| EXAMPLE NO. | PROMOTER AND MOLE RATIO | METHACRYLIC ACID % YIELD | % SELECTIVITY | % CONVERSION |
|---|---|---|---|---|
| 141 | Ag$_{0.6}$ | 55.1 | 55.1 | 100 |
| 142 | Cd$_{0.3}$ | 50.4 | 50.5 | 99.8 |
| 143 | Ce$_{0.2}$ | 51.3 | 51.3 | 100 |
| 144 | Dy$_{0.2}$ | 54.7 | 55.0 | 99.5 |
| 145 | La$_{0.2}$ | 55.6 | 55.6 | 100 |
| 146 | Mn$_{0.3}$ | 46.1 | 55.5 | 83 |
| 147 | Ni$_{0.3}$ | 44.9 | 44.9 | 100 |
| 148 | Ti$_{0.15}$ | 63.7 | 64.1 | 99.3 |
| 149 | U$_{0.15}$ | 40.6 | 40.8 | 99.6 |
| 150 | Zr$_{0.15}$ | 48.5 | 48.5 | 100 |

We claim:
1. A catalyst composition represented by the formula

$$A_aFe_bP_cO_x$$

wherein
A is selected from the group Cd, Cr, Ge, Th, Ti, U, Zr, rare earths and mixtures thereof; and
wherein
a is greater than zero but less than or equal to 1.0
b=0.75–1.5
c=1.0–2.0, and
x is the number of oxygens needed to satisfy the valence requirements of the remaining elements.

2. A catalyst as in claim 1 wherein said rare earths are selected from the group La, Ce, Nd, Sm, Eu, Dy, Ho, Tm, Yb and Lu.

3. A catalyst as in claim 1 wherein a is about 0.15 to about 0.5.

4. A catalyst as in claim 1 wherein said catalyst contains thorium.

5. A catalyst as in claim 1 wherein said catalyst contains uranium.

6. A catalyst as in claim 1 wherein said catalyst additionally contains inert diluents.

7. A catalyst as in claim 1 wherein said catalyst is coated upon a support.

8. A catalyst as in claim 1 wherein said catalyst contains at least one rare earth element.

9. A catalyst composition represented by the formula $$A_aFe_bP_cAg_dMn_dO_x$$

wherein
A is selected from the group Cd, Cr, Ge, Te, Th, Ti, U, Zr, rare earths and mixtures thereof; and
wherein
a=0–1.0
b=0.75–1.5
c=1.0–2.0
d is greater than zero and the total amount of Ag and Mn ranges from about 0.2 to 2.0, and
x is the numeral of oxygens needed to satisfy the valence requirements of the remaining elements.

10. A catalyst as in claim 9 wherein said catalyst is $Fe_{1.0}P_{1.84}Ag_{0.4}Mn_{0.4}O_x$.

11. A catalyst composition represented by the formula $$A_aFe_bP_cMn_dO_x$$

wherein
A is selected from the group Cd, Cr, Ge, Te, Th, Ti, U, Zr, rare earths and mixtures thereof; and
wherein
a=0.15–1.0
b=0.75–1.5
c=1.0–2.0
d=0.2–2.0, and
x is the number of oxygens needed to satisfy the valence requirements of the remaining elements.

12. A catalyst composition as in claim 11 wherein said A element is Te.

* * * * *

UNITED STATES PATENT AND TRADEMARK OFFICE
CERTIFICATE OF CORRECTION

PATENT NO. : 4,742,035

DATED : May 3, 1988

INVENTOR(S) : S. Erik Pederson et al

It is certified that error appears in the above-identified patent and that said Letters Patent is hereby corrected as shown below:

Title page: "Primary Examiner - J. Fitchett"
should read -- Primary Examiner - W. Shine --.

Signed and Sealed this

Twentieth Day of December, 1988

Attest:

DONALD J. QUIGG

*Attesting Officer*  *Commissioner of Patents and Trademarks*